United States Patent
Omotowa

(10) Patent No.: US 7,645,912 B2
(45) Date of Patent: *Jan. 12, 2010

(54) PROCESSES FOR PRODUCING HYDROFLUOROCARBON COMPOUNDS USING INORGANIC FLUORIDE

(75) Inventor: Bamidele Omotowa, Idaho Falls, ID (US)

(73) Assignee: International Isotopes, Inc., Idaho Falls, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/853,521

(22) Filed: Sep. 11, 2007

(65) Prior Publication Data

US 2008/0262276 A1   Oct. 23, 2008

Related U.S. Application Data

(60) Provisional application No. 60/912,571, filed on Apr. 18, 2007.

(51) Int. Cl.
*C07C 19/08* (2006.01)

(52) U.S. Cl. .................................................... 570/170

(58) Field of Classification Search ........................ None
See application file for complete search history.

(56) References Cited

U.S. PATENT DOCUMENTS

| | | | |
|---|---|---|---|
| 4,070,439 A | 1/1978 | Osaka et al. | |
| 4,876,406 A * | 10/1989 | Foulletier | 570/165 |
| 5,091,602 A | 2/1992 | Park et al. | |
| 5,399,549 A | 3/1995 | Felix et al. | |
| 5,399,796 A | 3/1995 | Correia et al. | |
| 5,446,216 A | 8/1995 | Rao | |
| 5,545,770 A | 8/1996 | Rao | |
| 5,831,136 A | 11/1998 | Rao | |
| 5,841,006 A | 11/1998 | Cuzzato et al. | |
| 5,918,106 A | 6/1999 | Bulko et al. | |
| 6,074,985 A | 6/2000 | Elsheikh et al. | |
| 6,127,586 A | 10/2000 | Scott et al. | |
| 6,229,058 B1 | 5/2001 | Sievert et al. | |
| 6,232,514 B1 | 5/2001 | Cuzzato et al. | |
| 6,268,541 B1 | 7/2001 | Kono et al. | |
| 6,392,106 B1 | 5/2002 | Kono et al. | |
| 6,433,233 B1 | 8/2002 | Kanemura et al. | |
| 6,479,718 B1 | 11/2002 | Elsheikh et al. | |
| 6,503,865 B1 | 1/2003 | Kanemura et al. | |
| 6,841,705 B2 | 1/2005 | Yuichi et al. | |
| 7,067,707 B2 | 6/2006 | Piepho et al. | |
| 7,071,368 B1 | 7/2006 | Merkel et al. | |
| 7,074,973 B2 | 7/2006 | Nappa et al. | |
| 2001/0049457 A1 * | 12/2001 | Stephens | 570/123 |
| 2008/0262274 A1 | 10/2008 | Omotowa | |
| 2008/0262275 A1 | 10/2008 | Omotowa | |
| 2008/0262277 A1 | 10/2008 | Omotowa | |

OTHER PUBLICATIONS

Okazaki et al., Kogyo Kagaku Zasshi (1969), 72(3), 630-3.*
Park et al., Kongop Hwahak (1993), 4(2), 318-23.
Schumb, W.C., "Some Metathetical Reactions of the Gaseous Fluorides of Group IV," Journal of the American Chemical Society, vol. 74, Jun. 1951, pp. 1754-1760.

(Continued)

*Primary Examiner*—Karl J Puttlitz
(74) *Attorney, Agent, or Firm*—Perkins Coie LLP

(57) ABSTRACT

Methods and systems for producing hydrofluorocarbon with an inorganic fluoride (e.g., germanium tetrafluoride ($GeF_4$)) are disclosed herein.

26 Claims, 6 Drawing Sheets

OTHER PUBLICATIONS

U.S. NonFinal Office Action dated Mar. 14, 2008 under U.S. Appl. No. 11/853,541, 8 pages.

U.S. NonFinal Office Action dated Mar. 14, 2008 under U.S. Appl. No. 11/853,557, 8 pages.

U.S. NonFinal Office Action dated Mar. 14, 2008 under U.S. Appl. No. 11/853,572, 8 pages.

Christe et al. Silicon Tetrafluoride, a New Fluorinating Agent, 1964, J. Org. Chem., p. 3007-3009.

International Search Report and Written Opinion; International Application No. PCT/US08/75133; Filed Sep. 3, 2008; Applicant: International Isotopes Inc.; Mailed Nov. 24, 2008, 10 pages.

International Search Report and Written Opinion; International Application No. PCT/US08/59929; Filed Apr. 10, 2008; Applicant: International Isotopes Inc.; Mailed Sep. 29, 2008, 10 pages.

International Search Report and Written Opinion; International Application No. PCT/US08/59933; Filed Apr. 10, 2008; Applicant: International Isotopes Inc.; Mailed Aug. 25, 2008, 10 pages.

International Search Report and Written Opinion; International Application No. PCT/US08/59942; Filed Apr. 10, 2008; Applicant: International Isotopes Inc.; Mailed Sep. 12, 2008, 9 pages.

International Search Report and Written Opinion; International Application No. PCT/US08/59937; Filed Apr. 10, 2008; Applicant: International Isotopes Inc.; Mailed Aug. 25, 2008, 9 pages.

U.S. Appl. No. 12/203,654, filed Sep. 3, 2008, Omotowa.

* cited by examiner

PROCESSES FOR PRODUCING HYDROFLUOROCARBON COMPOUNDS USING INORGANIC FLUORIDE

CROSS-REFERENCE TO RELATED APPLICATION

This application claims priority to Provisional U.S. Patent Application No. 60/912,571, entitled "Processes for Production of Hydrofluorocarbon Using Inorganic Fluoride From Pentachloroethane,", filed Apr. 18, 2007, the disclosure of which is incorporated herein by reference in its entirety. This application is also related to U.S. patent application Ser. No. 11/853,572, entitled "Processes for Producing Halogenated Hydrocarbon Compounds Using Inorganic Fluoride", U.S. patent application Ser. No. 11/583,541, entitled "Processes for Producing Chlorofluorocarbon Compounds Using Inorganic Fluoride", and U.S. patent application Ser. No. 11/853,557, entitled "Processes for Producing Halocarbon Compounds Using Inorganic Fluoride", the disclosures of which are incorporated herein by reference in their entirety.

TECHNICAL FIELD

The present disclosure is related to processes for producing halogenated hydrocarbon compounds (e.g., hydrofluorocarbon compounds). In particular, the present disclosure is related to processes for producing 1,2-substituted haloalkanes, such as 1,1,2,2,2-pentafluoroethane (HFC-125) and/or 1-chloro-1,2,2,2-tetrafluoroethane (HCFC-124).

BACKGROUND

Chlorofluorocarbon (CFC) and hydrochlorofluorocarbon (HCFC) compounds have been used as refrigerants, fire extinguishing agents, propellants, and solvents since the early twentieth century. However, CFC and HCFC are now believed to deplete the ozone layer of the earth via UV-promoted reactions. As a result, the U.S. Environmental Protection Agency has already banned the production and importation of certain CFC and HCFC products.

Internationally, the Montreal Protocol has set out plans for replacing CFC and HCFC compounds with hydrofluorocarbon (HFC) compounds. However, the cost of producing HFC compounds is considerably higher than that of producing CFC or HCFC compounds. Presently, industrial fluorination processes for producing HFC are based on hydrogen fluoride (HF) fluorination of chlorocarbons. FIG. 1 presents examples of known potential multistep routes to produce HFC-125.

As illustrated in FIG. 1, HFC-125 can be produced with either 1,1,2-trichloroethene (triclene) or 1,1,2,2-tetrachloroethene (perclene) using multistep processes. For example, HFC-125 can be produced by first converting either triclene or perclene into 1,1-dichloro-2,2,2-trifluoroethane (HCFC-123) and then fluorinating HCFC-123 to 1-chloro-1,2,2,2-tetrafluoroethane (HCFC-124). HFC-125 can then be produced by performing chlorine-fluorine exchange on HCFC-124 with hydrogen fluoride.

The processes for producing HFC-125 are more complex, both chemically and operationally, than those for CFC and HCFC compounds. Moreover, both the triclene and perclene processes require disposing of hydrogen chloride (HCl) byproducts. Procedures and equipment are available to convert some of the HCl byproducts into a chlorine ($Cl_2$) gas and subsequently recycle the chlorine gas back into the production process. Nonetheless, this recycling operation adds to the cost of the overall HFC production process. Therefore, there is a need to develop more efficient and cost-effective processes for producing HFC compounds such as HFC-125.

DETAILED DESCRIPTION

Figure 1:
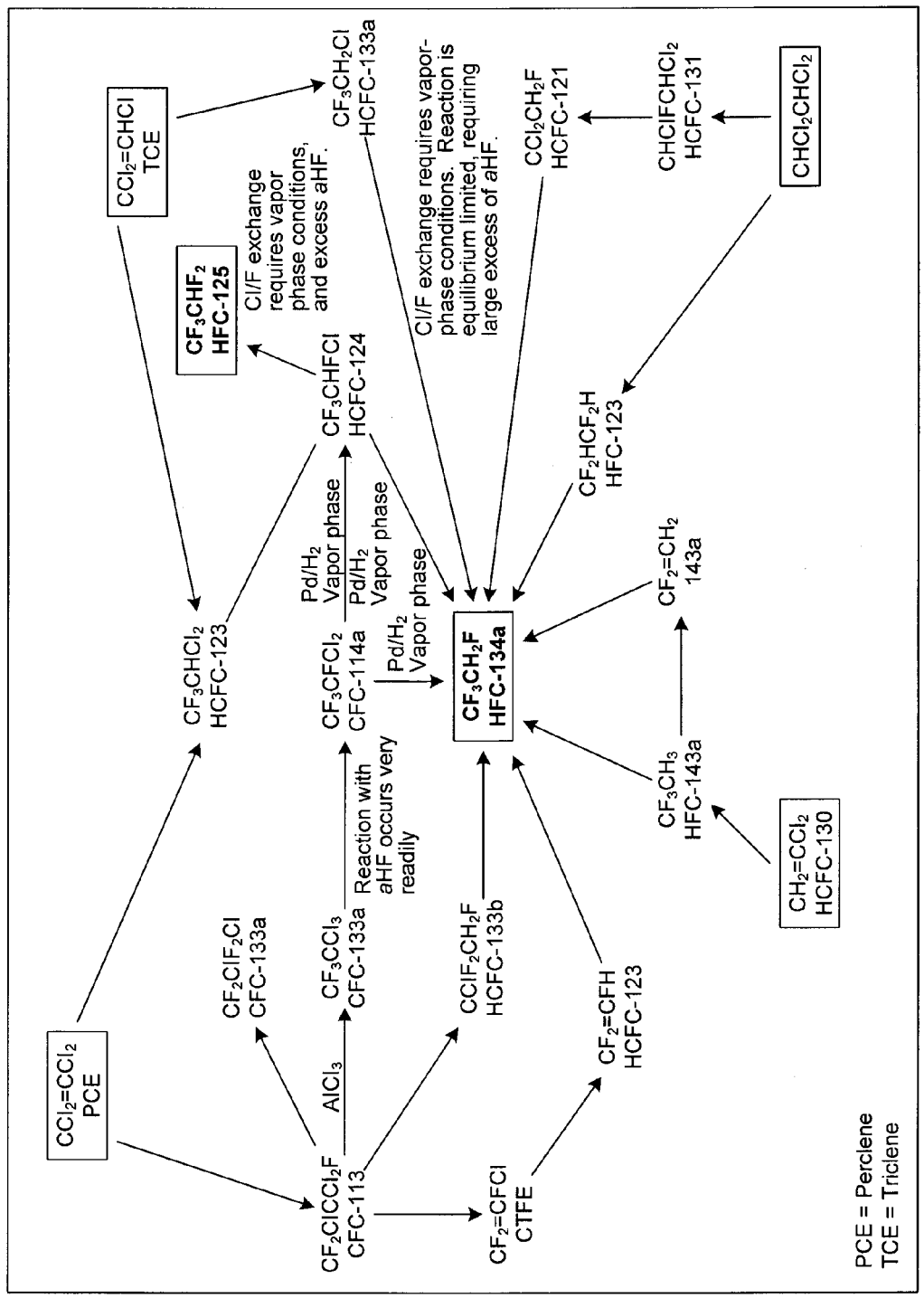
FIG. 1 is a schematic diagram illustrating potential routes to HFC-125 and HFC-134a in accordance with the prior art.

Specific details of several embodiments of the disclosure are described below with reference to processes for efficiently and cost-effectively producing halogenated hydrocarbon compounds. The term "halogenated hydrocarbon compounds" generally refers to halogen-substituted (e.g., fluorine-, chlorine-, bromine-, and/or iodine-substituted) organic compounds containing carbon and hydrogen. Examples of halogenated hydrocarbon compounds include hydrofluorocarbon compounds containing fluorine, carbon, and hydrogen, hydrochlorocarbon compounds containing chlorine, carbon, and hydrogen, and hydrochlorofluorocarbon compounds containing fluorine, chlorine, carbon, and hydrogen. Several other embodiments of the invention may have different configurations, components, or procedures than those described in this section. A person of ordinary skill in the art, therefore, will accordingly understand that the invention may have other embodiments with additional elements, or the invention may have other embodiments without several of the elements shown and described below.

One aspect of the present disclosure is directed to the use of an inorganic fluoride as a fluorinating agent for producing hydrofluorocarbon (HFC) compounds, in particular, HFC-125 ($F_2CHCF_3$). The following description uses $GeF_4$ as an example of an inorganic fluoride to show various embodiments of the fluorination reaction of the present disclosure for illustration purposes. However, a skilled artisan will appreciate that $GeF_4$ is merely an example of an inorganic fluoride. Other inorganic fluoride for use in the systems and processes can include at least one of bromine trifluoride ($BrF_3$), manganese tetrafluoride ($MnF_4$), sulfur tetrafluoride ($SF_4$), bromine pentafluoride ($BrF_5$), and tungsten hexafluoride ($WF_6$).

Another aspect of the present disclosure relates to producing HFC-125 by employing starting materials effective to produce HFC-125 in the fewest number of reaction steps. In one embodiment, the present disclosure relates to producing HFC-125 from 1,1,2,2,2-pentachloroethane (referred to as pentachloroethane hereinafter) in one reaction step. The inventor has observed that the reaction described above has an unexpectedly high yield (about 70-75%) and a good selectivity (about 1.6 to 4.0) toward HFC-125, as described in more detail below with reference to the experimental results.

A further aspect of the present disclosure is directed to using one or more catalysts to catalyze a fluorination reaction between an inorganic fluoride and a chlorocarbon compound. It is believed that, in certain embodiments, the class of compounds known as superacids and/or Lewis acids can catalyze such fluorination reaction. The term "superacid" generally refers to an acid with an acidity greater than that of 100% sulfuric acid ($H_2SO_4$). Examples of superacids include trifluoromethane sulfonic acid ($CF_3SO_3H$) and fluorosulfuric acid ($FSO_3H$). The term "Lewis acid" generally refers to a compound that is an electrophile or an electron acceptor. Examples of Lewis acids include aluminum trichloride ($AlCl_3$), iron trichloride ($FeCl_3$), boron trifluoride ($BCl_3$), niobium pentachloride ($NbCl_5$), and the lanthanide triflates, e.g., ytterbium(III) triflate. In certain embodiments, aluminum trichloride ($AlCl_3$) can be used to react with $GeF_4$ to form $AlCl_xF_y$ (x+y=3), in situ, which has been observed to catalyze the $GeF_4$ fluorination of chlorocarbons. In other embodiments, $SbCl_3$, $SbF_5$, $SbF_3$, $AsF_5$, $AsCl_3$, $TaCl_5$, $TaF_5$, $NbCl_5$, $NbF_5$, $HSO_3F$, $CF_3SO_3F$, $Cr_2O_3$, and/or other suitable superacids and/or Lewis acids can also be used to catalyze a fluorination of chlorocarbons in the presence of, e.g., $GeF_4$.

Reaction Systems

Figure 2:
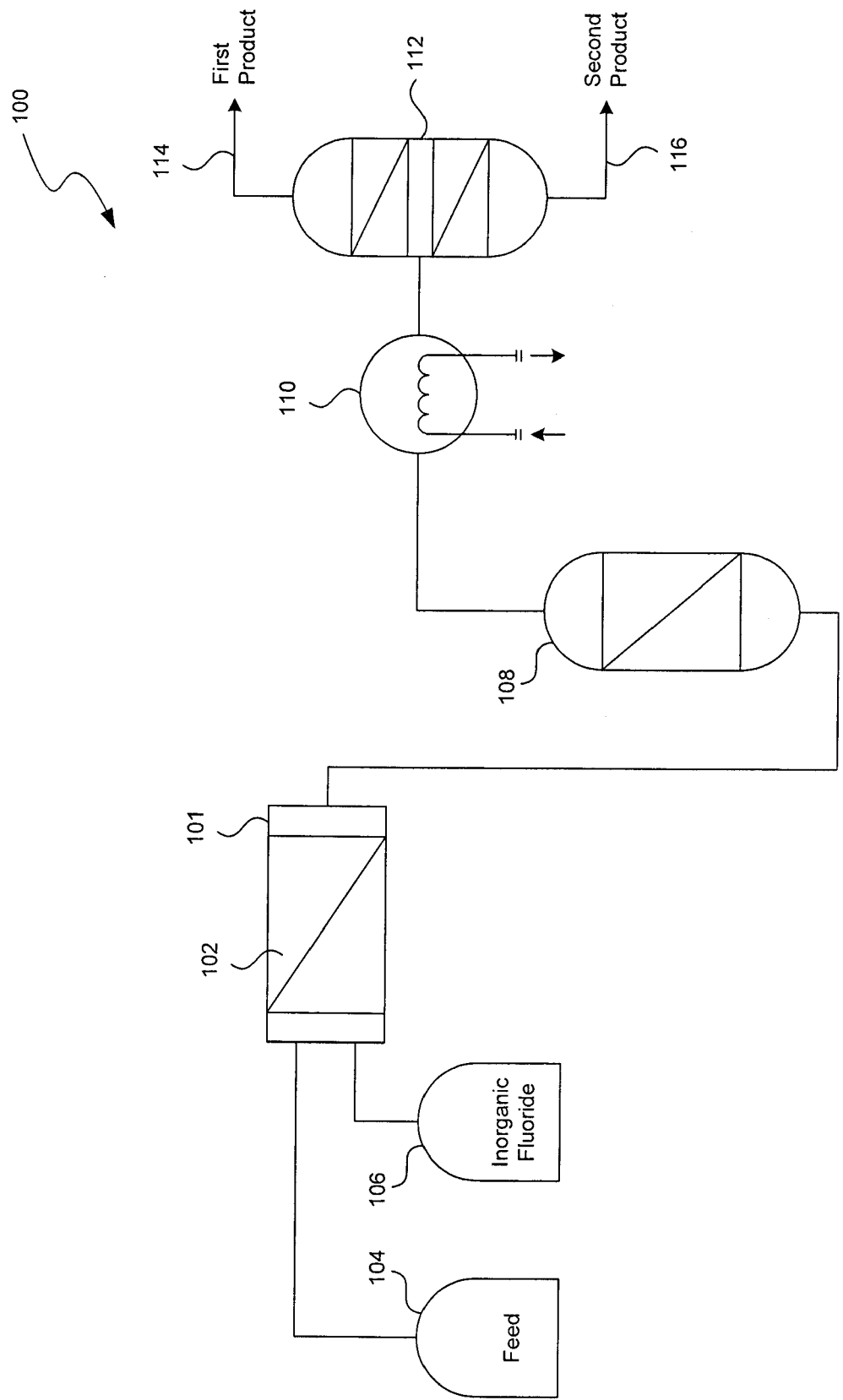
FIG. 2 is a schematic diagram illustrating a system for producing halogenated hydrocarbon compounds in accordance with an embodiment of the disclosure.

FIG. 2 is a schematic diagram illustrating a system 100 for producing HFC-125 in accordance with an embodiment of the disclosure. The system 100 can include a reactor 101 operatively coupled to a feed storage 104 containing, e.g., pentachloroethane, and an inorganic fluoride storage 106 containing, e.g., $GeF_4$. The reactor 101 can be configured generally as a tubular reactor constructed from Inconel, Hastelloy, and/or other fluorine-resistant material. In some embodiments, the reactor 101 can include a catalyst bed 102 containing $AlCl_3$ or other suitable catalyst. In other embodiments, the catalyst bed 102 can be omitted from the reactor 101, and a catalyst (e.g., $AlCl_3$) can be fed into the reactor 101 during operation.

The system 100 can include a scrubber 108 that receives a reaction product from the reactor 101. The scrubber 108 can be configured to remove impurities and/or unreacted material from the product. For example, in one embodiment, the scrubber 108 includes a liquid base containing, e.g., potassium hydroxide (KOH), sodium hydroxide (NaOH), and/or other base for absorbing, reacting, and/or otherwise combining with unreacted inorganic halide (e.g., $GeF_4$). In another embodiment, the scrubber 108 includes a solid base (e.g., pellets) containing KOH, NaOH, and/or other base. In further embodiments, the scrubber 108 can include both a liquid base and a solid base for removing unreacted halide.

The system 100 can also include an optional product trap 110 downstream of the scrubber 108 for collecting HFC and/or HCFC compounds from the reaction product. In the illustrated embodiment, the product trap 110 is configured as a heat exchanger that can cool the reaction product with a coolant (e.g., liquid nitrogen). In some embodiments, heat exchange with the coolant substantially condenses the HFC and/or HCFC compounds in the reaction product. In other embodiments, only a portion of the HFC and/or HCFC compounds (e.g., materials with low boiling points) is condensed.

The system 100 can further include a separator 112 downstream of the optional product trap 110. The separator 112 can be configured to split HFC and/or HCFC compounds in the reaction product. In the illustrated embodiment, the separator 112 includes a distillation column that can produce a first product from a top end 114 and a second product from a bottom end 116. In other embodiments, the separator 112 can also include a flash tank, a cyclone, and/or other liquid-liquid separation/liquid-gas separation devices. In further embodiments, instead of producing the first and second products from the top end 114 and the bottom end 116, the separator 112 can also produce products from locations intermediate the top end 114 and the bottom end 116 based on the volatility profile of the reaction product.

In operation, the reactor 101 first receives a reaction feed containing, for example, pentachloroethane from the feed storage 104 and an inorganic fluoride (e.g., $GeF_4$) from the inorganic fluoride storage 106. In one embodiment, $GeF_4$ can be in the stoichiometric amount required to fluorinate pentachloroethane in the reaction feed. For example, the molar ratio of $GeF_4$ to pentachloroethane can be about 1.12:1. In other embodiments, $GeF_4$ can be in molar excess of the stoichiometric amount required. For example, the molar ratio of $GeF_4$ to pentachloroethane in the reaction feed can be from about 2:1 to about 4:1.

In the reactor 101, $GeF_4$ and pentachloroethane in the reaction feed contact the catalyst (e.g., $AlCl_3$) held in the catalyst bed. The reactor 101 can be at a temperature of about 220° to about 375° C. and at a pressure of about 500 to 800 psig (i.e., about 3.45 MPa to about 5.52 MPa). Under such temperature and pressure conditions, the inventor has observed that pentachloroethane and $GeF_4$ in the reaction feed can react to form HFC-125 and HCFC-124 with high yield and good selectivity toward HFC-125. Other potential fluorination products such as 1,2,2,2-tetrachloro-1-fluoroethane ($CHClFCCl_3$), 1,1,2,2-tetrachloro-1-fluoroethane ($CHCl_2CCl_2F$), 1,2,2-trichloro-1,2-difluoroethane ($CHClFCCl_2F$), 1,1,1-trichloro-2,2-difluoroethane ($CHF_2CCl_3$), 1,1-dichloro-2,2,2-trifluoroethane ($CHCl_2CF_3$), 1,2-dichloro-1,2,2-trifluoroethane ($CHClFCClF_2$), 1-chloro-1,1,2,2-tetrafluoroethane ($CHF_2CClF_2$), 1,1,2-trichloro-2,2-difluoroethane ($CHCl_2CClF_2$), or other hydrohalocarbon compounds were not observed.

There have been prior unsuccessful attempts to use $GeF_4$ for fluorination of chlorocarbons such as pentachloroethane. The inventor has recognized that those prior experiments failed, at least in part, because of the omission of an appropriate catalyst. The inventor has also recognized $AlCl_3$ and/or other Lewis acid catalysts can cause $GeF_4$ to readily react with pentachloroethane. Without being bound by theory, it is believed that $GeF_4$ can first react with $AlCl_3$ to form a series of equilibria between $AlCl_3$ and $GeF_4$ as follows:

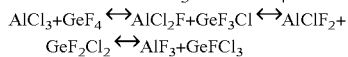

It is believed that the $AlCl_xF_y$ (x+y=3) compounds may then act as Lewis acid catalysts to lower the activation energy for fluorinating pentachloroethane. It is also believed that $AlF_3$ is a more efficient catalyst than $AlCl_2F$ and/or $AlClF_2$. Thus, in some embodiments, the reaction equilibria can be shifted toward $AlF_3$ by, for example, adding excess $GeF_4$ to the reaction feed, removing products from the reaction, and/or using other suitable techniques.

In one embodiment, the reaction described above can be carried out in a batch mode. For example, the reaction conditions can be maintained in the reactor 101 until the reaction is complete, and then the reaction product can be discharged from the reactor 101 to the scrubber 108. In other embodiments, the reaction described above can be carried out in a continuous mode. For example, the reactor 101 can be configured as a plug-flow reactor, a constantly stirred tank reactor, and/or other types of reactor with sufficient residence time to allow the completion of the reaction in a continuous operation.

After the reaction is complete, the reaction product flows from the reactor 101 to the scrubber 108 for removing impurities and/or unreacted material from the product. For example, the scrubber 108 can remove GeCl$_4$ from other gaseous material in the reaction product. In another example, if GeF$_4$ is in molar excess of pentachloroethane in the reaction feed, some GeF$_4$ is likely to remain after the reaction is complete. In one embodiment, the scrubber 108 can contain KOH and/or NaOH that reacts with the excess GeF$_4$ in order to purify the reaction product. In other embodiments, the scrubber 108 can remove the excess GeF$_4$ using other physical and/or chemical techniques.

The reaction product can then pass through the optional product trap 110 for collecting HFC and/or HCFC products. In the illustrated embodiment, the reaction product exiting the scrubber 108 includes a gas containing HFC-125 and HCFC-124. When the reaction product passes through the product trap 110, HFC-125 and HCFC-124 compounds in the reaction product substantially condense by a coolant (e.g., liquid nitrogen) at the product trap 110. In other embodiments, the product trap 110 can include a refrigeration unit, an isotropic expander, an isenthalpic expander, and/or other cooling techniques for condensing HFC-125 and HCFC-124 compounds. In further embodiments, the system 100 can operate at a sufficient pressure (e.g., 1000 psig) such that the reaction product is at least partially a liquid at the outlet of the scrubber 108, and the product trap 110 can be omitted.

After the reaction product is substantially condensed, the separator 112 splits HFC-125 from HCFC-124 to produce the first product containing essentially HFC-125 from the top end 114 and the second product containing essentially HCFC-124 from the bottom end 116. At one atmospheric pressure, HFC-125 has a boiling point of −48° C., and HCFC-124 has a boiling point of −12° C. As a result, the relative volatility between HFC-125 and HCFC-124 is sufficient to enable a ready separation between these two compounds.

Fluorination reaction carried out in the system 100 described above can efficiently and cost-effectively produce HFC-125 and/or other hydrofluorocarbon compounds. Unlike conventional techniques having multiple reaction steps, using the system 100 can produce HFC-125 in one reaction step via direct chlorine-fluorine exchange on pentachloroethane. The reaction has been observed to produce an unexpectedly high yield of at least about 70%, more preferably at least about 75%, and even more preferably at least about 80%. The reaction has also been observed to produce a good selectivity of at least about 1.6, more preferably about 2.4, and even more preferably about 4.0 toward HFC-125. Moreover, the reaction, in one embodiment, has been observed to produce only HFC-125 and HCFC-124, which have sufficiently different volatility to enable ready separation of the reaction product.

Even though the system 100 described above has a one-pass configuration, in certain embodiments, the system 100 can also have at least one recycle loop. For example, in some embodiments, unreacted reaction feed and/or other compounds can be recycled back to the reactor 101.

Method for Producing Halogenated Hydrocarbon Compounds

Figure 3:
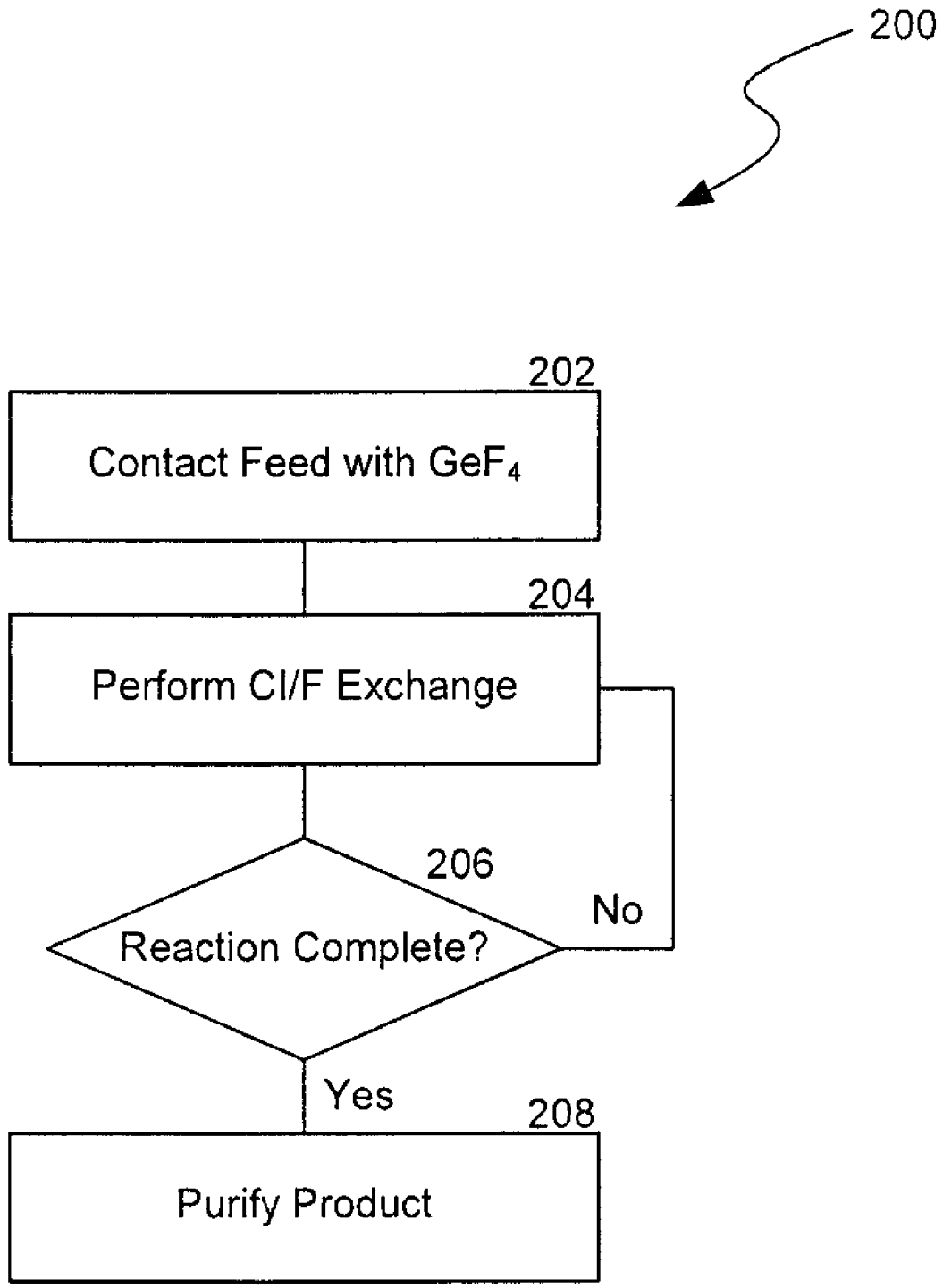
FIG. 3 is a flow chart illustrating a method for producing halogenated hydrocarbon compounds in accordance with an embodiment of the disclosure.

FIG. 3 is a flow chart illustrating a method 200 for producing halogenated hydrocarbon compounds (e.g., HFC-125) in accordance with an embodiment of the disclosure. The method 200 can include contacting a reaction feed containing pentachloroethane with GeF$_4$ in the presence of a catalyst (e.g., AlCl$_3$) at block 202. The molar ratio of AlCl$_3$/pentachloroethane/GeF$_4$ can be about 1:A:B (2<A<15 and 4<B<60 while B:A is greater than 2). The method 200 then includes performing chlorine-fluorine exchange on pentachloroethane at block 204 as follows:

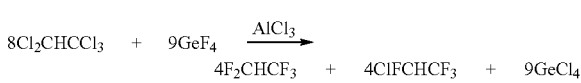

Suitable reaction temperatures can be about 220° to about 375° C., and suitable pressures can be about 500 to 800 psig.

A decision is made at block 206 to determine whether the reaction is complete. In one embodiment, the decision can be based on a reaction time (e.g., 6-8 hours). In another embodiment, the decision can be based on a conversion of the reaction and/or other reaction parameters. For example, an operator can periodically sample the material in the reactor 101 to determine a concentration of pentachloroethane. If the concentration of pentachloroethane is below a threshold, then the reaction is indicated to be complete.

If the reaction is complete, the method 200 further includes purifying the reaction product at block 208. Purifying the reaction product can include separating HFC-125 and HCFC-124 of the reaction product using condensation, distillation, liquid-liquid extraction, liquid-gas separation, and/or other suitable techniques. If the reaction is not complete, the process reverts to performing the chlorine-fluorine exchange on pentachloroethane at block 204.

EXAMPLES

Figure 4:
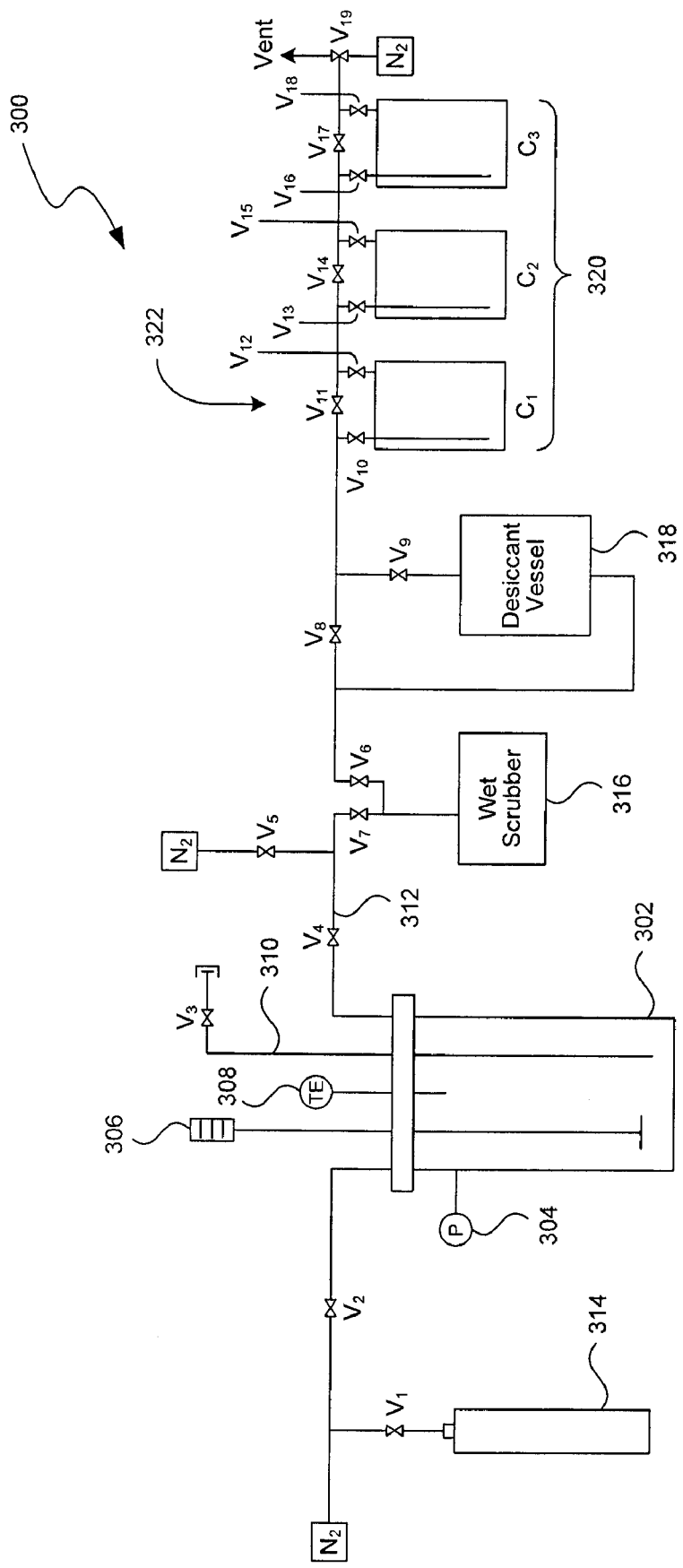
FIG. 4 is a schematic diagram illustrating a system for producing halogenated hydrocarbon compounds in accordance with an embodiment of the disclosure.

Experiments were conducted to fluorinate pentachloroethane using GeF$_4$ in the presence of AlCl$_3$ in a bench-top reactor (Model No. 4563) supplied by the Parr Instrument Company of Moline, Ill. FIG. 4 is a schematic diagram illustrating an experimental system 300 for producing HFC-125 in accordance with an embodiment of the disclosure.

As shown in FIG. 4, the system 300 includes an Inconel 600 reactor 302 having a volume of about 600 mL. The reactor 302 includes a pressure monitor 304, a mixer 306, and a temperature monitor 308. The reactor 302 also includes a liquid sample line 310 and a gas sample line 312. The system 300 also includes a cylinder 314 holding gaseous GeF$_4$ (187 psig at 21° C.). The system 300 also includes a 200 mL wet scrubber 316 containing KOH and a desiccant vessel 318 containing Al$_2$O$_3$ and KOH pellets. The system 300 further includes three 75 mL sampling cylinders 320 (labeled C$_1$-C$_3$). The sampling cylinders 320 can be held at various temperatures and pressures for collecting materials with different boiling points. Various components of the system 300 can be isolated using a plurality of valves 322 (labeled V$_1$-V$_{19}$).

All chemicals used in the following experiments were obtained commercially from Aldrich-Sigma, Inc. of Milwaukee, Wis. The GeF$_4$ gas was produced by International Isotopes, Inc. of Idaho Falls, Id. Fourier transform infrared (FTIR) spectra were recorded on a MIDAC I1201 bench-top infrared spectrometer as neat liquids between potassium bromide (KBr) plates or gas samples in a 10 cm path-length demountable gas cell with zinc-selenium (ZnSe) windows. 1H, 13C, and 19F NMR spectra were obtained on a 300 MHz Bruker AMX spectrometer at 200, 50, and 188 MHz, respectively, by using CDCl$_3$ as a locking solvent. Chemical shifts were reported relative to Me$_4$Si or CFCl$_3$. GC-MS spectra were obtained with a Shimadzu Q5050 spectrometer (EI-mode). Elemental analyses were performed by the Desert Analytics Laboratory of Tucson, Ariz.

Experiment I

Liquid pentachloroethane (25.8 g, 0.127 mol) and solid aluminum chloride (4.0 g, 0.030 mol, boiling point=194° C.) were charged into the reactor 302. The reactor 302 was closed and bolted. $GeF_4$ gas (48.6 g, 0.327 mol) was fed into the reactor 302 at 21° C. from the cylinder 314 in a vented hood. The pressure of the reactor was 184 psig. The gas-in and gas-out valves on the reactor were closed to isolate the reagents in the vessel. The supply sample line was purged with nitrogen several times and then disconnected.

The reactor 302 was then transferred into a heating mantle and connected to a manifold in fluid communication with the wet scrubber 316, the desiccant vessel 318, the sampling cylinders 320, and a vent/vacuum system. The heating mantle was programmed to warm the stirred reagents at 340° C. The pressure in the reactor 302 rose to 795 psig at 340° C. After 8 hours, the reactor 302 was slowly cooled to room temperature. As a result, the pressure dropped to 100 psig at 21° C. The reduced pressure suggested that a significant amount of $GeF_4$ had reacted to produce either solid or liquid phase products.

The gaseous products, including unreacted $GeF_4$, were vented through the gas-out valve to the wet scrubber 316 until the pressure in the reactor 302 dropped to about 0 psig. The reaction byproducts were recovered as insoluble germanium (IV) oxide. Subsequently, the reactor 302 was pressurized several times with nitrogen to 90 psig and then vented through the wet scrubber 316.

The fluorinated gaseous products were then collected in one of the sampling cylinders 320 cooled to −196° C. with liquid nitrogen. The crude product was subsequently separated by cryogenic distillation and identified by comparing FTIR spectra with appropriate literature references. The products were identified as 80% HFC-125 and 20% HCFC-124. The total gas pressure in the sampling cylinder 320 was 20 psig, indicating a 9% product collection.

On opening the reactor 302, 4.8 g of unreacted liquid pentachloroethane was recovered from the reactor 302 after hydrolysis of fuming $GeCl_4$ content of the crude product. This is indicative that as much as about 20 g of the starting pentachloroethane must have been converted.

Experiment II

Another experiment was carried out following a procedure similar to that of Experiment I with a different molar ratio of the reagents. In particular, liquid pentachloroethane (18.3 g, 0.0904 mol) and solid aluminum chloride (3.7 g, 0.0277 mol) were charged into the reactor 302. $GeF_4$ gas (33.6 g, 0.226 mol) were then was fed into the reactor 302. The reactor 302 was then heated to 340° C., and the pressure in the reactor 302 rose to 490 psig. After 8 hours, the reactor 302 was slowly cooled to room temperature. As a result, the pressure dropped to 85 psig at 21° C.

Experimental Results

Pentachloroethane reacted readily with $GeF_4$. As shown in the FTIR analysis results in FIGS. 5 and 6, the reaction produced only HFC-125 and HCFC-124 in both Experiments I and II, while other potential fluorinating products were not observed. The results from cryogenic distillation and FTIR analysis of the reaction product and selected reaction conditions of Experiments I and II above are listed in the table below.

| Reaction | Molar Ratio ($AlCl_3$/C—Cl/$GeF_4$) | Yield | Condition (P/T/Time) | Product Selectivity | |
|---|---|---|---|---|---|
| | | | | HCFC-124 | HFC-125 |
| Exp. I | 1:4:11 | 70% | 500 psig/ 340° C./8 hr | 20% | 80% |
| Exp. II | 1:3:8 | 75% | 490 psig/ 340° C./8 hr | 37.5% | 62.5% |

Figure 5:
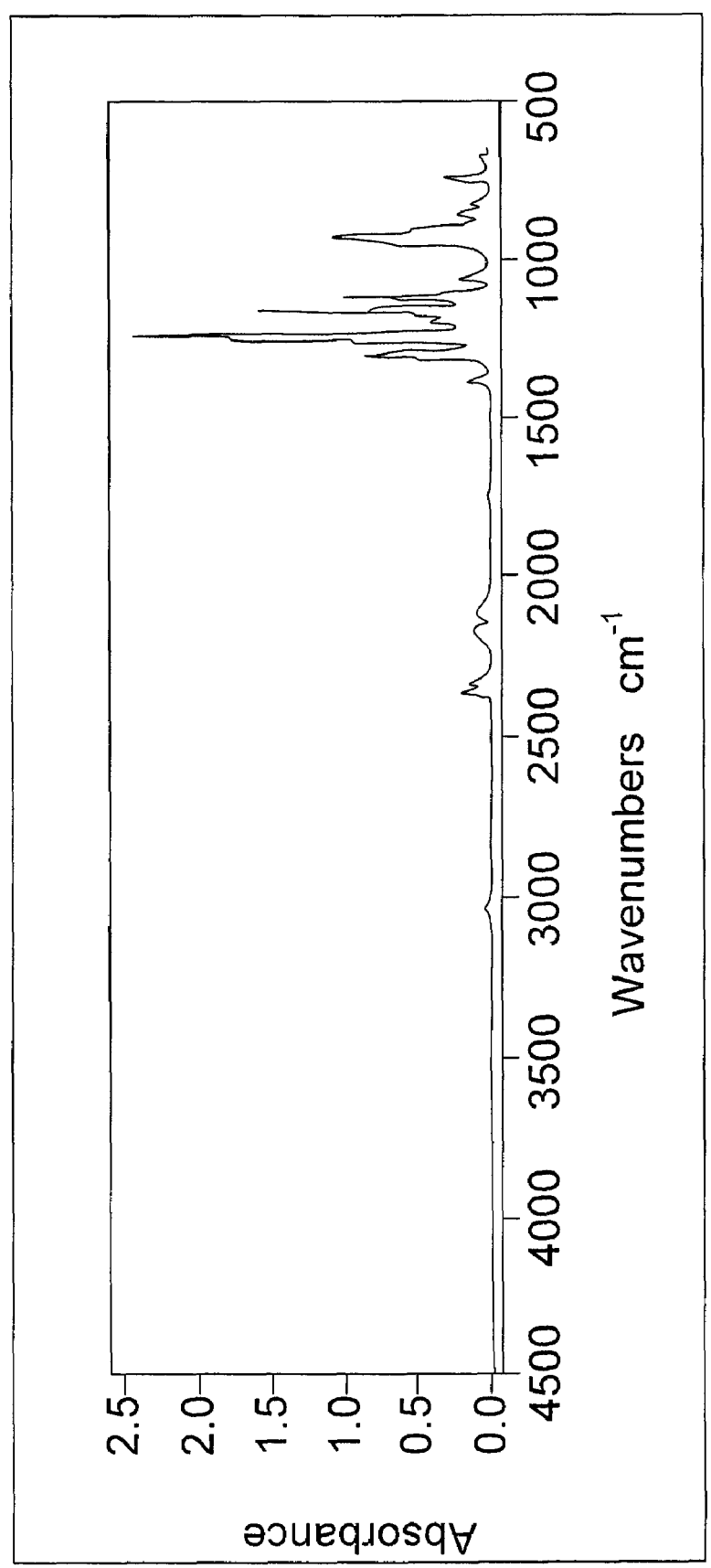
FIG. 5 is a Fourier transform infrared (FTIR) scan of a reaction product prepared in accordance with an embodiment of the disclosure.
Figure 6:
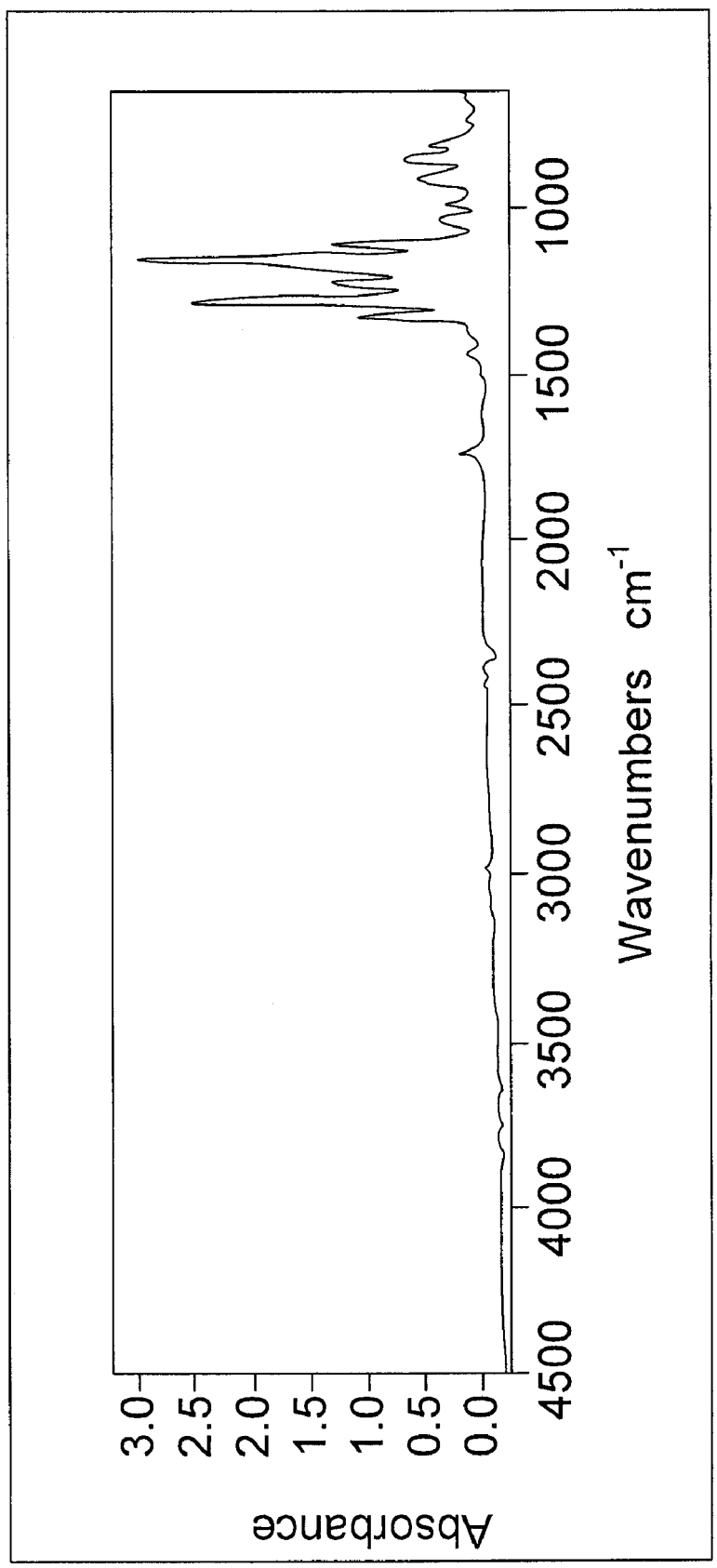
FIG. 6 is a Fourier transform infrared (FTIR) scan of a reaction product prepared in accordance with another embodiment of the disclosure.

As can be seen from the table above and FIGS. 5 and 6, both Experiments I and II produced HFC-125 with high yield (i.e., ≧ about 70%, or ≧ about 75%) and good selectivity (i.e., at least about 62.5% and up to about 80%) toward HFC-125 from inexpensive non-fluorinated starting material. Moreover, the inventor has observed that $GeF_4$ reacted with trace moisture to clean the $AlCl_3$ catalyst surface, and catalyst deactivation was not observed. As a result, high temperature catalyst pretreatment can be eliminated.

From the foregoing, it will be appreciated that specific embodiments of the invention have been described herein for purposes of illustration, but that various modifications may be made without deviating from the invention. Elements of one embodiment may be combined with other embodiments in addition to or in lieu of the elements of the other embodiments. Accordingly, the invention is not limited except as by the appended claims.

I claim:

1. A method for producing a hydrofluorocarbon compound, comprising reacting 1,1,2,2,2-pentachloroethane ($Cl_2CHCCl_3$) with germanium tetrafluoride ($GeF_4$) in the presence of an aluminum (Al) halide.

2. The method of claim 1 wherein reacting 1,1,2,2,2-pentachloroethane ($Cl_2CHCCl_3$) with germanium tetrafluoride ($GeF_4$) includes reacting 1,1,2,2,2-pentachloroethane with germanium tetrafluoride in the presence of aluminum trichloride ($AlCl_3$).

3. The method of claim 2 wherein reacting 1,1,2,2,2-pentachloroethane ($Cl_2CHCCl_3$) with germanium tetrafluoride ($GeF_4$) includes reacting 1,1,2,2,2-pentachloroethane with germanium tetrafluoride in the presence of aluminum trichloride at a temperature of about 220°-375° C.

4. The method of claim 2 wherein reacting 1,1,2,2,2-pentachloroethane ($Cl_2CHCCl_3$) with germanium tetrafluoride ($GeF_4$) includes reacting 1,1,2,2,2-pentachloroethane with germanium tetrafluoride in the presence of aluminum trichloride at a pressure of about 500 to 800 psig.

5. The method of claim 2, further comprising reacting germanium tetrafluoride with aluminum trichloride to form at least one of aluminum chlorodifluoride ($AlClF_2$), aluminum dichlorofluoride ($AlCl_2F$), and aluminum trifluoride ($AlF_3$).

6. The method of claim 5, further shifting the equilibrium toward aluminum trifluoride.

7. The method of claim 2, further comprising maintaining a molar ratio of germanium tetrafluoride to aluminum trichloride about 2 to about 15.

8. The method of claim 2, further comprising maintaining a molar ratio of germanium tetrafluoride to 1,1,2,2,2-pentachloroethane about 1 to about 4.

9. The method of claim 2, further comprising producing at least one of 1,1,2,2,2-pentafluoroethane and 1-chloro-1,1,2,2-tetrafluoroethane ($CHF_2CClF_2$) without producing at least one of 1,2,2,2-tetrachloro-1-fluoroethane ($CHClFCCl_3$), 1,1,2,2-tetrachloro-1-fluoroethane ($CHCl_2CCl_2F$), 1,2,2- trichloro-1,2-difluoroethane (CHClFCCl$_2$F), 1,1,1-trichloro-2,2-difluoroethane (CHF$_2$CCl$_3$), 1,1-dichloro-2,2,2-trifluoroethane (CHCl$_2$CF$_3$), 1,2-dichloro-1,2,2-trifluoroethane (CHClFCClF$_2$), 1-chloro-1,1,2,2-tetrafluoroethane (CHF$_2$CClF$_2$), and 1,1,2-trichloro-2,2-difluoroethane (CHCl$_2$CClF$_2$).

10. A method for producing hydrofluorocarbon compounds, comprising contacting a reaction feed containing 1,1,2,2,2-pentachloroethane (Cl$_2$CHCCl$_3$) and germanium tetrafluoride (GeF$_4$) with a catalyst containing aluminum trichloride (AlCl$_3$) in a reactor, reacting 1,1,2,2,2-pentachloroethane in the reaction feed with germanium tetrafluoride in the presence of the catalyst, and selectively producing a reaction product consisting essentially of 1,1,2,2,2-pentafluoroethane (F$_2$CHCF$_3$) and 1-chloro-1,2,2,2-tetrafluoroethane (ClFCHCF$_3$).

11. The method of claim 10 wherein contacting a reaction feed includes contacting the reaction feed with a catalyst bed of the reactor, the catalyst bed holding the catalyst containing aluminum trichloride.

12. The method of claim 10 wherein reacting 1,1,2,2,2-pentachloroethane with germanium tetrafluoride includes performing chlorine-fluoride exchange on 1,1,2,2,2-pentachloroethane of the reaction feed in the presence of the catalyst.

13. The method of claim 10 wherein reacting 1,1,2,2,2-pentachloroethane with germanium tetrafluoride includes reacting 1,1,2,2,2-pentachloroethane with germanium tetrafluoride at a temperature of about 220° C. to about 350° C. and a pressure of about 500 to about 800 psig.

14. The method of claim 10 wherein reacting 1,1,2,2,2-pentachloroethane with germanium tetrafluoride includes reacting 1,1,2,2,2-pentachloroethane with germanium tetrafluoride having a molar ratio of about 1:3:8 for aluminum chloride/1,1,2,2,2-pentachloroethane/germanium tetrafluoride.

15. The method of claim 10 wherein reacting 1,1,2,2,2-pentachloroethane with germanium tetrafluoride includes reacting 1,1,2,2,2-pentachloroethane with germanium tetrafluoride having a molar ratio of about 1:4:11 for aluminum chloride/1,1,2,2,2-pentachloroethane/germanium tetrafluoride.

16. The method of claim 10 wherein reacting 1,1,2,2,2-pentachloroethane with germanium tetrafluoride includes reacting 1,1,2,2,2-pentachloroethane with germanium tetrafluoride while germanium tetrafluoride is in molar excess over 1,1,2,2,2-pentachloroethane, and wherein the method further includes scrubbing excess germanium tetrafluoride with a material containing potassium hydroxide and/or sodium hydroxide.

17. The method of claim 10 wherein reacting 1,1,2,2,2-pentachloroethane with germanium tetrafluoride includes reacting 1,1,2,2,2-pentachloroethane with germanium tetrafluoride while germanium tetrafluoride is in molar excess over 1,1,2,2,2-pentachloroethane, and wherein the method further includes recovering excess germanium tetrafluoride in the reaction feed and recycling the recovered excess germanium tetrafluoride to the reactor.

18. The method of claim 10 wherein producing a reaction product includes producing a reaction product containing hydrohalocarbon compounds consisting essentially of 1,1,2,2,2-pentafluoroethane (F$_2$CHCF$_3$) and 1-chloro-1,2,2,2-tetrafluoroethane (ClFCHCF$_3$).

19. The method of claim 10, further comprising distilling the produced reaction product containing 1,1,2,2,2-pentafluoroethane and 1-chloro-1,2,2,2-tetrafluoroethane and separating 1,1,2,2,2-pentafluoroethane from 1-chloro-1,2,2,2-tetrafluoroethane in the reaction product.

20. A method for producing hydrofluorocarbon compounds, comprising:
    loading a charge containing 1,1,2,2,2-pentachloroethane (Cl$_2$CHCCl$_3$) and aluminum trichloride (AlCl$_3$) into a reactor;
    flowing a feed gas containing germanium tetrafluoride (GeF$_4$) into the reactor; and
    reacting 1,1,2,2,2-pentachloroethane of the charge with germanium tetrafluoride of the feed gas in the presence of aluminum trichloride in the reactor.

21. The method of claim 20, further comprising discharging a product gas containing 1,1,2,2,2-pentafluoroethane (F$_2$CHCF$_3$) and 1-chloro-1,2,2,2-tetrafluoroethane (ClFCHCF$_3$) from the reactor.

22. The method of claim 21, further comprising collecting the product gas in a sample cylinder cooled with liquid nitrogen.

23. The method of claim 20, further comprising heating the reactor to a temperature of about 220° C. to about 350° C. before flowing the feed gas into the reactor.

24. The method of claim 20 wherein reacting 1,1,2,2,2-pentachloroethane of the charge with germanium tetrafluoride of the feed gas includes reacting 1,1,2,2,2-pentachloroethane with germanium tetrafluoride with a conversion greater than about 70%.

25. The method of claim 20 wherein reacting 1,1,2,2,2-pentachloroethane of the charge with germanium tetrafluoride of the feed gas includes reacting 1,1,2,2,2-pentachloroethane with germanium tetrafluoride with a conversion greater than about 70% and a selectivity greater than about 60% for 1,1,2,2,2-pentafluoroethane.

26. The method of claim 20 wherein reacting 1,1,2,2,2-pentachloroethane includes concurrently forming a series of equilibria between species of AlCl$_x$F$_y$ (x+y=3) and species of GeCl$_a$F$_b$ (a+b=4) and fluorinating 1,1,2,2,2-pentachloroethane in the charge with germanium tetrafluoride while catalyzed by the species of AlCl$_x$F$_y$ (x+y=3) with a selectivity toward 1,1,2,2,2-pentafluoroethane (F$_2$CHCF$_3$) and 1-chloro-1,2,2,2-tetrafluoroethane (ClFCHCF$_3$).

* * * * *